(12) United States Patent
Srinivasan et al.

(10) Patent No.: US 11,007,313 B2
(45) Date of Patent: May 18, 2021

(54) PEN NEEDLE MAGAZINE

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 374 days.

(21) Appl. No.: 16/095,885

(22) PCT Filed: Mar. 31, 2017

(86) PCT No.: PCT/US2017/025378
§ 371 (c)(1),
(2) Date: Oct. 23, 2018

(87) PCT Pub. No.: WO2017/189170
PCT Pub. Date: Nov. 2, 2017

(65) Prior Publication Data
US 2019/0125959 A1    May 2, 2019

Related U.S. Application Data

(60) Provisional application No. 62/328,680, filed on Apr. 28, 2016.

(51) Int. Cl.
*A61M 5/00* (2006.01)
*A61M 5/32* (2006.01)
(Continued)

(52) U.S. Cl.
CPC .......... *A61M 5/002* (2013.01); *A61M 5/3202* (2013.01); *A61M 5/3205* (2013.01);
(Continued)

(58) Field of Classification Search
CPC .......... A61M 2005/312; A61M 5/3204; A61M 5/3202; A61M 2005/004; A61M 5/3295;
(Continued)

(56) References Cited

U.S. PATENT DOCUMENTS 5,829,589 A    11/1998  Nguyen et al.
5,873,462 A    2/1999   Nguyen et al.
(Continued)

FOREIGN PATENT DOCUMENTS

EP    2119423 A1    11/2009
EP    2420270 A2    2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC

(57) ABSTRACT

An attachable needle assembly (2) used on a medication delivery pen (4), the needle assembly (2) comprising a communication needle (10) configured to pierce a reservoir septum of the medication delivery pen (4), a spike housing (8) surrounding the communication needle (10) and configured to engage the medication delivery pen (4), a selector ring (16), including a selector opening (18), enclosing a septum (22, 30) of the needle assembly (2) defining a septum chamber (28, 29) that is in fluid communication with the
(Continued)

communication needle (10), a plurality of needles (34) disposed in the septum (22, 30) of the needle assembly (2), and a peel tab (60) enclosing each of the plurality of needles (34), wherein the selector opening (18) is aligned with a selected peel tab (60) corresponding to a selected needle (40), the selected peel tab (60) is drawn out of the selector ring (16) and moves the selected needle (40) from a first position to a second position, and the selected needle (40) enters into fluid communication with the communication needle (10) in the second position.

22 Claims, 12 Drawing Sheets

(51) Int. Cl.
　　*A61M 5/34* 　　　(2006.01)
　　*A61B 50/30* 　　　(2016.01)
(52) U.S. Cl.
　　CPC ............ *A61M 5/3297* (2013.01); *A61M 5/34* (2013.01); *A61B 50/3001* (2016.02); *A61M 5/3295* (2013.01); *A61M 2005/004* (2013.01)
(58) Field of Classification Search
　　CPC .... A61M 5/34; A61M 5/3297; A61M 5/3213; A61M 5/002
　　See application file for complete search history.

(56) References Cited

U.S. PATENT DOCUMENTS

| | | |
|---|---|---|
| 5,931,817 A | 8/1999 | Nguyen et al. |
| 8,876,780 B2 | 11/2014 | Bruehwiler et al. |
| 9,101,724 B2 | 8/2015 | Chapin et al. |
| 9,107,988 B2 | 8/2015 | Bruehwiler et al. |
| 9,155,838 B2 | 10/2015 | Bilton et al. |
| 9,381,303 B2 | 7/2016 | Abhijitsinh et al. |
| 9,717,860 B2 | 8/2017 | Bruehwiler et al. |
| 10,029,042 B2 | 7/2018 | Searle et al. |
| 2001/0014792 A1 | 8/2001 | West et al. |
| 2002/0020646 A1 | 2/2002 | Groth et al. |
| 2002/0020647 A1 | 2/2002 | Groth |
| 2005/0084631 A1 | 4/2005 | Anderson |
| 2008/0312604 A1 | 12/2008 | Boesen |
| 2010/0152660 A1 | 6/2010 | Mack et al. |
| 2010/0217206 A1 | 8/2010 | Lum et al. |
| 2011/0068034 A1 | 3/2011 | Hwang et al. |
| 2012/0004620 A1 | 1/2012 | Spool et al. |
| 2012/0016315 A1 | 1/2012 | Radmer et al. |
| 2012/0041373 A1* | 2/2012 | Bruehwiler ......... A61M 5/3243 604/173 |
| 2012/0041381 A1* | 2/2012 | Raj ....................... A61M 5/002 604/192 |
| 2012/0041383 A1 | 2/2012 | Bruehwiler et al. |
| 2012/0041390 A1 | 2/2012 | Spool et al. |
| 2012/0130313 A1 | 5/2012 | Byerly et al. |
| 2013/0041321 A1 | 2/2013 | Cross et al. |
| 2013/0053751 A1 | 2/2013 | Holtham |
| 2014/0076758 A1 | 3/2014 | Dasbach et al. |
| 2014/0123479 A1 | 5/2014 | Dasbach |
| 2014/0262884 A1 | 9/2014 | Priebe et al. |
| 2014/0299622 A1 | 10/2014 | Hofmann et al. |
| 2014/0339113 A1 | 11/2014 | Hofmann et al. |
| 2015/0025469 A1 | 1/2015 | Larsen et al. |
| 2015/0163898 A1 | 6/2015 | Mokhtarzad |
| 2015/0283333 A1 | 10/2015 | Butler et al. |
| 2015/0335827 A1 | 11/2015 | Stefansen et al. |
| 2015/0346184 A1 | 12/2015 | Galasso |
| 2016/0000992 A1 | 1/2016 | Steel et al. |
| 2016/0030683 A1 | 2/2016 | Taylor et al. |
| 2016/0074587 A1 | 3/2016 | Searle et al. |
| 2016/0082195 A1 | 3/2016 | Atterbury et al. |
| 2016/0106925 A1 | 4/2016 | Boesen |
| 2017/0106136 A1 | 4/2017 | DiBiasi |

FOREIGN PATENT DOCUMENTS

| | | |
|---|---|---|
| EP | 2586475 A1 | 5/2013 |
| EP | 2696913 B1 | 9/2015 |
| JP | 2013544153 A | 12/2013 |
| WO | 2008/150715 A1 | 12/2008 |
| WO | 2014/020001 A1 | 2/2014 |
| WO | WO-2014086684 A1 | 6/2014 |
| WO | 2015191457 A1 | 12/2015 |
| WO | 2016/050902 A1 | 4/2016 |

\* cited by examiner

PEN NEEDLE MAGAZINE

This application claims the benefit under 35 U.S.C. § 119(e) of U.S. Provisional Patent Application Ser. 62/328,680, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a needle assembly that is attachable to a medication delivery pen to provide a magazine of needles for use. Such a needle assembly provides advantages in separating a patient end and a non-patient end, and allows for engagement and disengagement to the medication delivery pen. Moreover, improvements in sterility, simplicity and safety are achieved by the needle assembly because none of the needles in the magazine pierce the septum of the medication delivery pen throughout operation, each needle only moves axially, each needle is used for injection one at a time and the needles are unable to be reused.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an attachable needle assembly for use on a medication delivery pen, the needle assembly comprising a communication needle that is configured to pierce a reservoir septum of the medication delivery pen, a spike housing surrounding the communication needle and configured to engage the medication delivery pen, a selector ring including a selector opening, the selector ring enclosing a septum of the needle assembly defining a septum chamber, the septum chamber of the needle assembly being in continuous fluid communication with the communication needle, a plurality of needles disposed in the septum of the needle assembly, and a peel tab enclosing each of the plurality of needles, wherein the selector opening of the selector ring is aligned with a selected peel tab of the plurality of peel tabs corresponding to a selected needle of the plurality of needles, the selected peel tab is drawn out of the selector ring and moves the selected needle from a first position of the needle assembly to a second position of the needle assembly, and the selected needle enters into fluid communication with the communication needle in the second position.

The foregoing and/or other aspects of the present invention can also be achieved by a method of operating an attachable needle assembly on a medication delivery pen, the method comprising piercing a reservoir septum of the medication delivery pen, engaging the medication delivery pen, establishing fluid communication between the medication delivery pen and the needle assembly, disposing a plurality of needles in a septum of the needle assembly, and enclosing each of the plurality of needles with a peel tab, wherein a portion of the needle assembly is aligned with a selected peel tab of the plurality of peel tabs corresponding to a selected needle of the plurality of needles, the selected peel tab is drawn out of the needle assembly and moves the selected needle from a first position of the needle assembly to a second position of the needle assembly, and the selected needle enters into fluid communication with the medication delivery pen in the second position.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
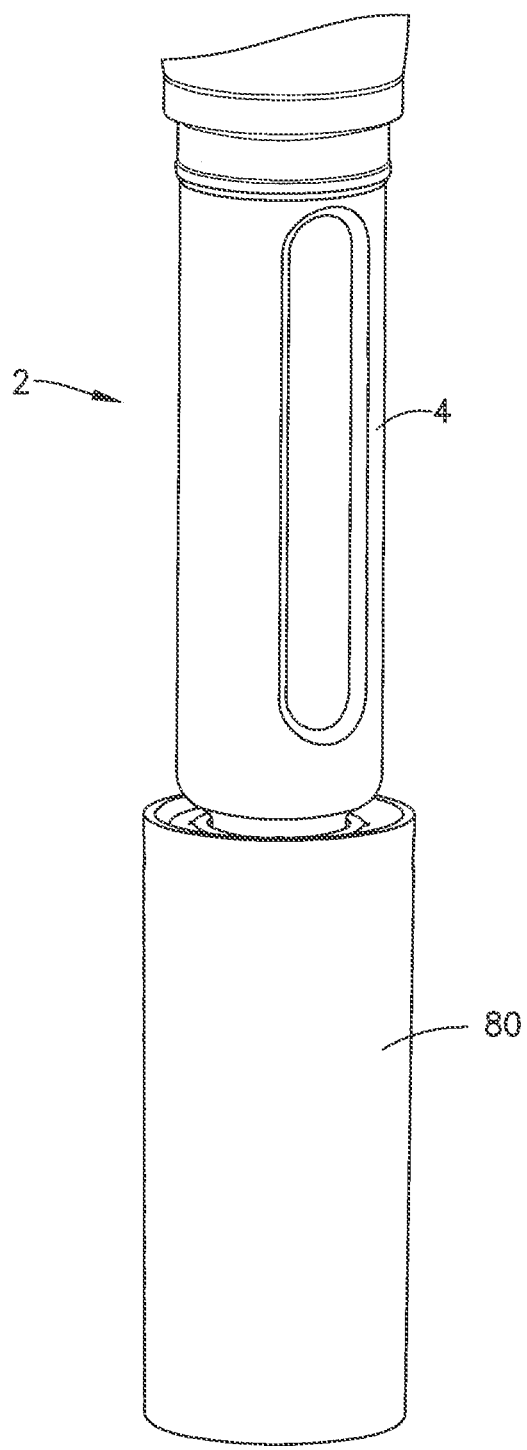
FIG. 1 illustrates a front elevation view of an exemplary medication delivery pen connected to a needle assembly.
Figure 2:
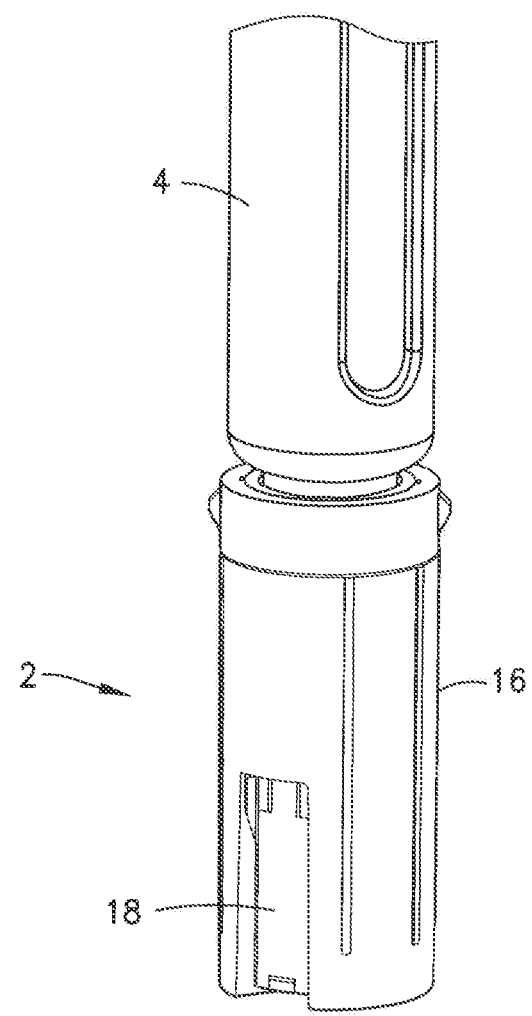
FIG. 2 illustrates a front elevation view of the medication delivery pen connected to the needle assembly with a cover removed.

FIG. 1 illustrates a medication delivery pen 4 used for injecting medicament, such as liquid drugs, into a living body. A needle assembly 2 is mounted on the medication delivery pen 4 to enhance medication delivery. A removable cover 80 encloses the needle assembly 2. FIG. 2 illustrates the cover 80 removed and exposing a selector ring 16 having a selector opening 18. Benefits and advantages of the needle assembly 2 including the removable cover 80 and the selector ring 16 are described below.

Figure 3:
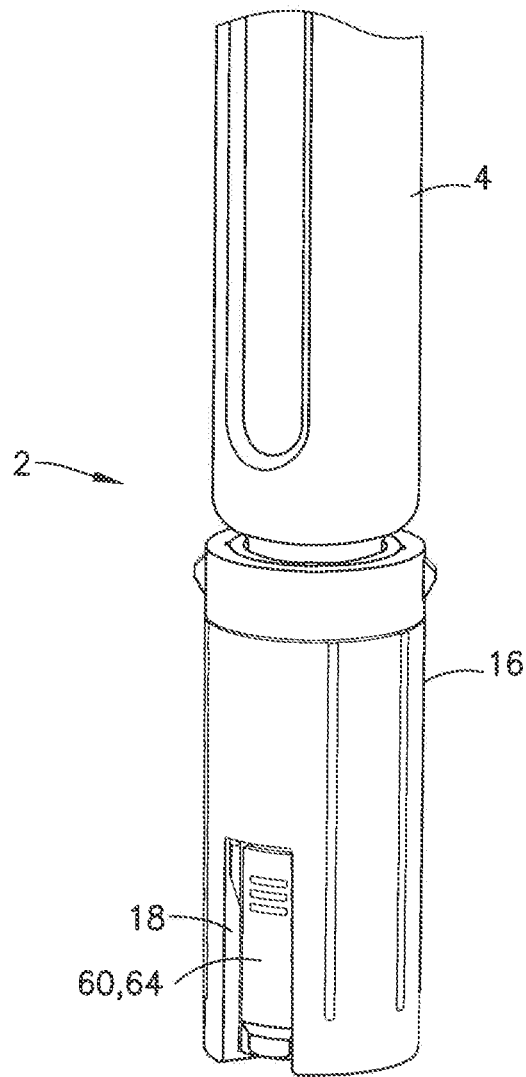
FIG. 3 illustrates a front elevation view of a first position of the needle assembly with a selector ring aligned to a peel tab.
Figure 4:
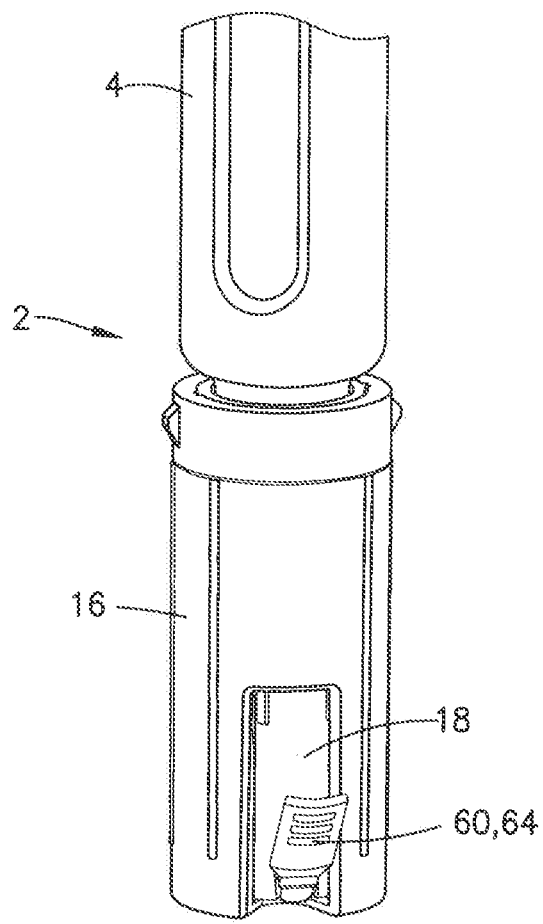
FIG. 4 illustrates a front elevation view of the peel tab being removed from the selector ring.

FIGS. 3 and 4, according to one embodiment, illustrate the selector ring 16 of the needle assembly 2. The selector ring 16 includes the selector opening 18. A user is able to rotate the selector ring 16 around the needle assembly 2 to access each needle. Specifically, the selector opening 18 is aligned to a peel tab 60 having a tab 64 that is attached to the needle. More information regarding these features is described below.

Figure 5:
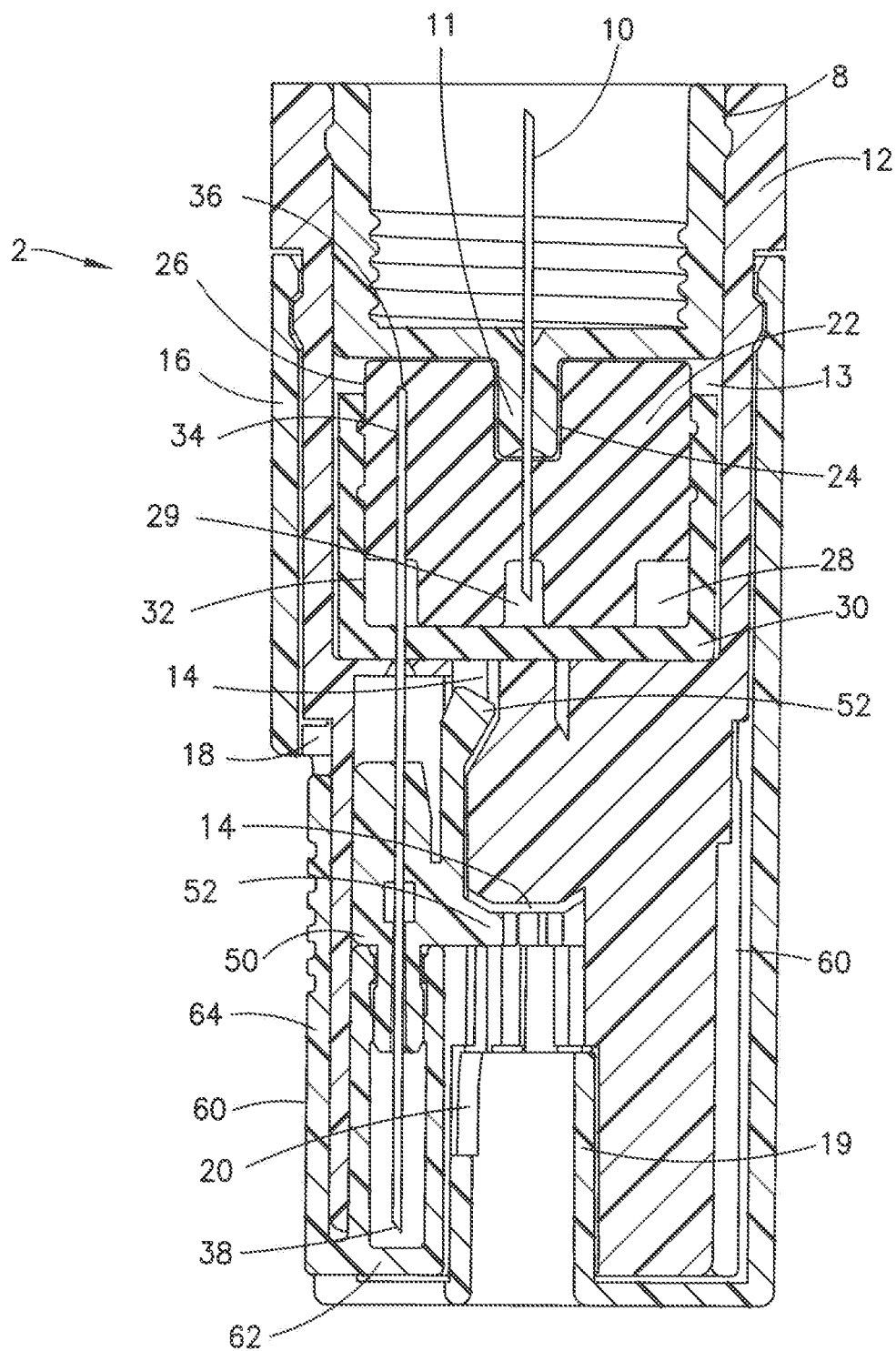
FIG. 5 illustrates a cross sectional view of the needle assembly of FIG. 3.

According to one embodiment, FIG. 5 illustrates a cross sectional view of a first position of the needle assembly 2 where none of a plurality of needles 34 are exposed for medicament delivery. The needle assembly 2 preferably includes a magazine of seven hollow needles, although greater or fewer needles are contemplated.

Figure 11:
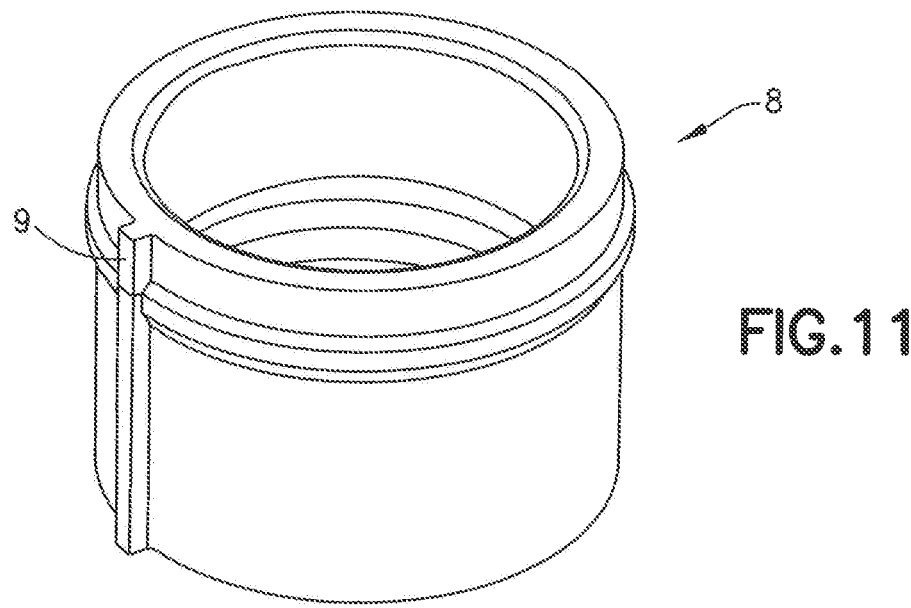
FIG. 11 illustrates a top perspective view of a spike housing.
Figure 12:
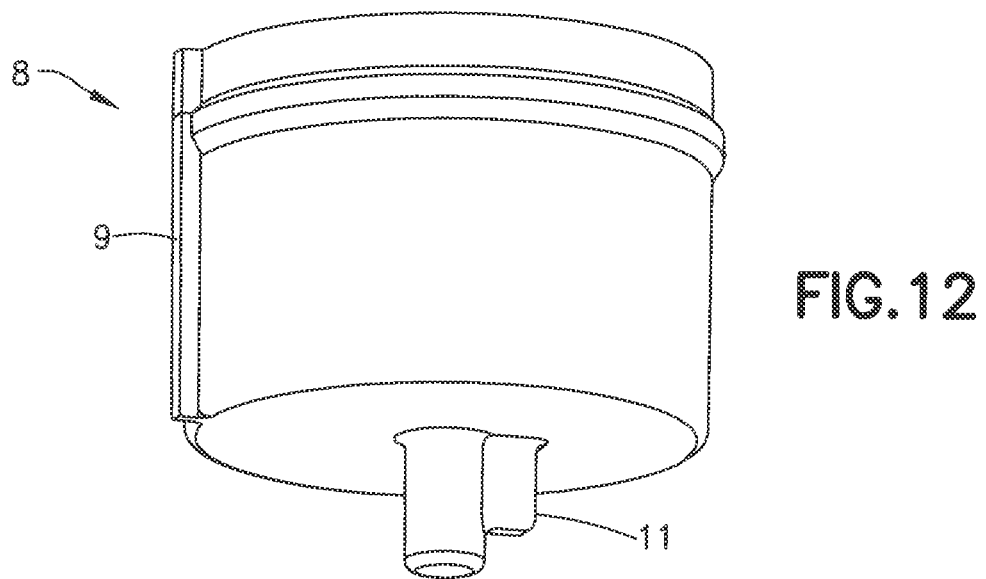
FIG. 12 illustrates a bottom perspective view of the spike housing.

The needle assembly 2 includes a spike housing 8 including an alignment protrusion 9 and a spike mounting protrusion 11 as illustrated in FIGS. 11 and 12. The spike housing 8 is configured to engage the medication delivery pen 4. For example, an inner wall of the spike housing 8 can be threaded to engage with threads on the medication delivery pen 4. Various other engagement means are contemplated.

The spike mounting boss 11 of the spike housing 8 is configured to engage a septum 22, 30 of the needle assembly 2. The spike mounting boss 11 is asymmetrical in shape for alignment purposes. Similarly, the alignment protrusion 9 of the spike housing 8 is asymmetrical in shape for alignment purposes when assembled to a frame 12.

A hollow communication needle 10 is disposed in the spike housing 8 and is preferably fixed to the spike mounting boss 11 by adhesive although other engagement means are contemplated. A sharpened proximal end of the communication needle 10 is configured to pierce a vial, cartridge or reservoir septum (not shown), for example, of the medication delivery pen 4 and establish fluid communication between a liquid medication-containing vial, cartridge or reservoir and the needle assembly 2.

As described above, the spike housing 8 is disposed in the frame 12. Specifically, the alignment protrusion 9 of the spike housing 8 is secured in a corresponding mating feature of the frame 12 for proper orientation. The frame 12 further includes a top cavity 13 and a bottom cavity 14 which houses the various components of the needle assembly 2.

The spike housing 8 is disposed in the top cavity 13 of the frame 12. The selector ring 16 encloses the frame 12.

The needle assembly 2, according to one embodiment, further includes a needle assembly septum 22, 30. The needle assembly septum 22, 30 is also disposed in the top cavity 13 of the frame 12. The needle assembly septum 22, 30 includes an inner septum 22 and an outer septum 30. The inner septum 22 is disposed within the outer septum 30.

Figure 15:
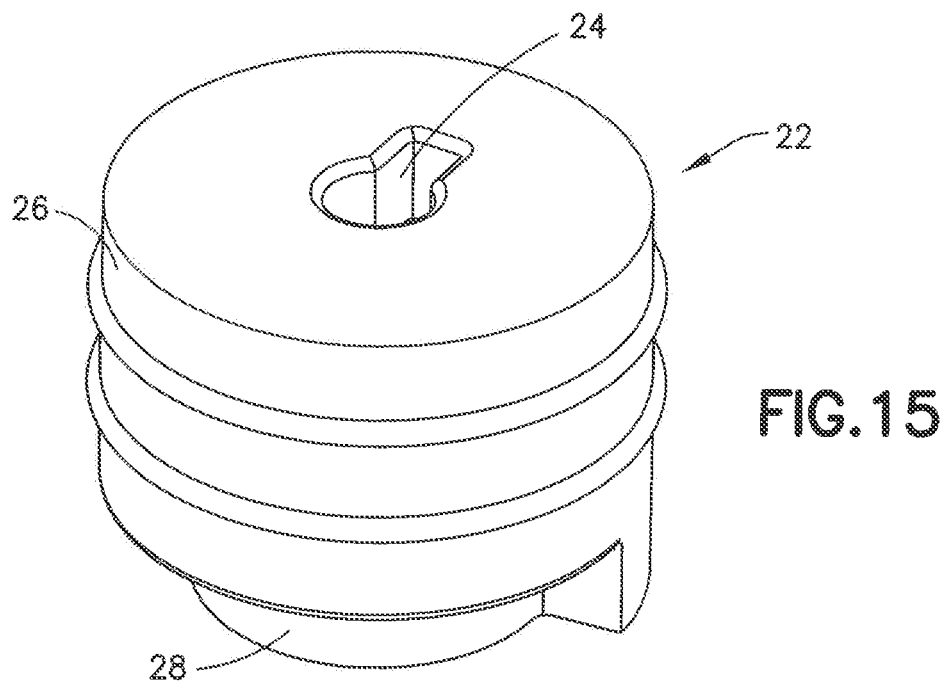
FIG. 15 illustrates a right perspective view of an inner septum.
Figure 16:
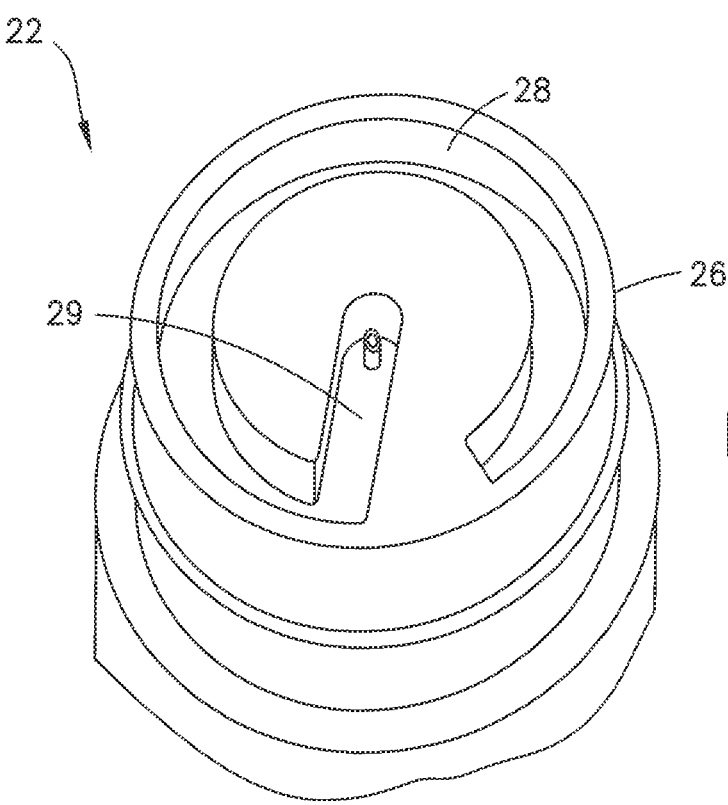
FIG. 16 illustrates a bottom perspective view of the inner septum.

As illustrated in FIGS. 15 and 16, the inner septum 22 includes an inner septum opening 24 that is disposed at a top surface of the inner septum 22 and travels through a centerline of the inner septum 22. The inner septum opening 24 is asymmetrically shaped to mate with the spike mounting boss 11 to engage the two components together in the needle assembly 2. Specifically, the inner septum opening 24 and the spike mounting boss 11 includes asymmetrical features of a key and a key hole to align and orient the two components together upon engagement. The communication needle 10 is disposed at the centerline of the inner septum opening 24 and the spike mounting boss 11. Accordingly, the reservoir of the medication delivery pen 4 communicates with the communication needle 10 and the inner septum 22 to allow liquid medicament to flow into the needle assembly 2.

FIG. 16 illustrates the inner septum 22 including a septum chamber 28, 29 comprising a continuous circular cavity 28 and a longitudinal cavity 29. The continuous circular cavity 28 or a curved recess is disposed on a bottom surface of the inner septum 22. Preferably, the circular cavity 28 extends continuously approximately 315°±30° around the bottom face of the inner septum 22 and adjacent to a circumferential edge of the inner septum 22. In an alternate embodiment, as illustrated in FIG. 15, the circular cavity 28 is an opening that extends through the outer circumferential edge of the inner septum 22. At one end point of the circular cavity 28, the longitudinal cavity 29 or longitudinal recess extends toward a center of the inner septum 22.

The communication needle 10 is in continuous fluid communication with the septum chamber 28, 29. Specifically, a sharpened distal end of the communication needle 10 is disposed in the longitudinal cavity 29 of the inner septum 22. Since the communication needle 10 is fixed to the spike housing 8, the communication needle 10 does not move during operation.

Figure 6:
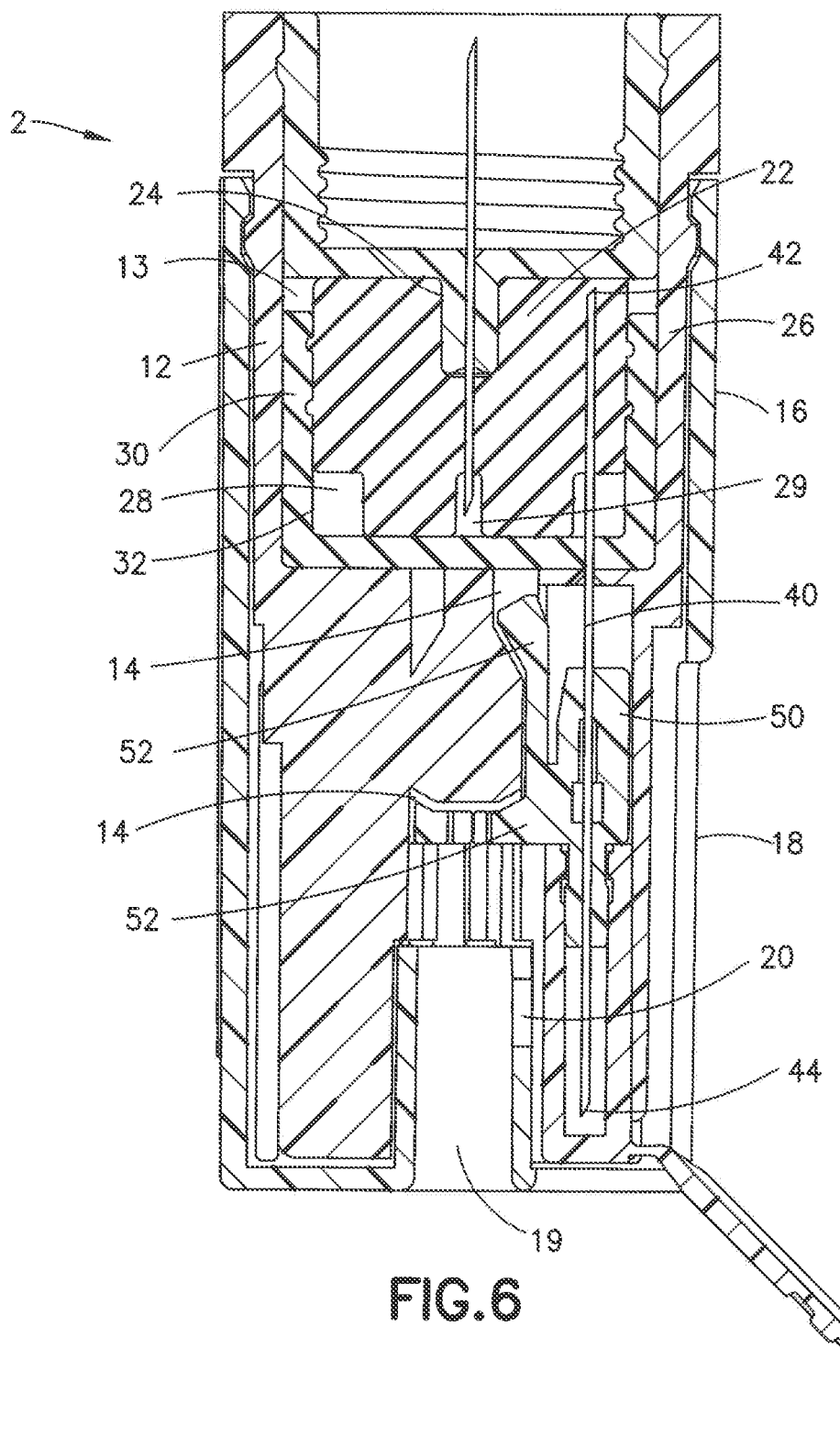
FIG. 6 illustrates a cross sectional view of the needle assembly of FIG. 4 with the peel tab extended downward.
Figure 7:
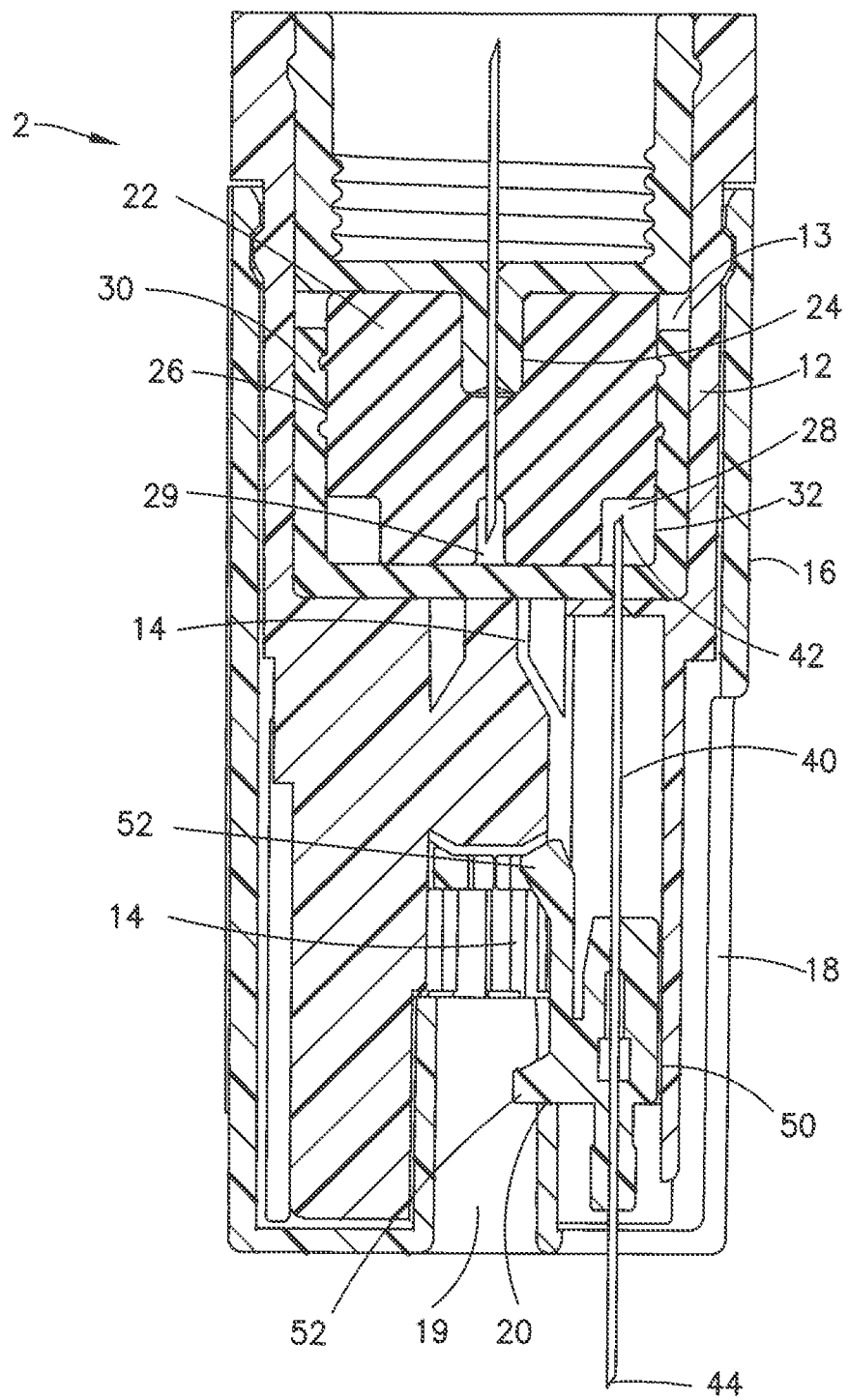
FIG. 7 illustrates a cross sectional view of a second position of the needle assembly.
Figure 14:
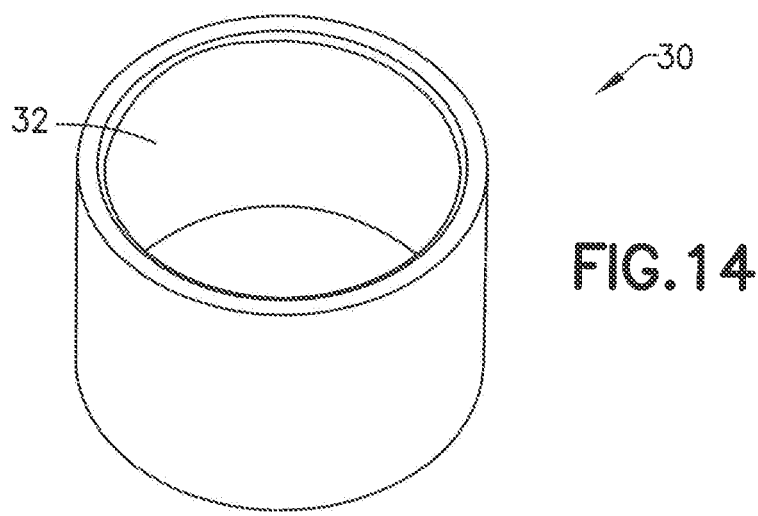
FIG. 14 illustrates a right perspective view of an outer septum.

FIG. 14 illustrates an inner diameter 32 of the outer septum 30. In assembly, as preferably illustrated in FIG. 5, the bottom face of the inner septum 22 is in direct sealing contact with the bottom surface of the outer septum 30. Alternatively, as illustrated in FIGS. 6 and 7, when the inner and outer septums are assembled 22, 30, a groove is created between the inner diameter 32 and the bottom surface of the outer septum 30 and the circular cavity 28 extending through the circumferential edge of the inner septum 22.

An outer diameter 26 of the inner septum 22 engages the inner diameter 32 of the outer septum 30 via an annular snap fit or an interference fit, for example, to seal and secure the needle assembly septum 22, 30. The inner septum 22 and the outer septum 30 are preferably composed of different materials having different durometers to enhance sealing characteristics. Accordingly, the longitudinal cavity 29 of the septum chamber 28, 29 establishes fluid communication with the inner septum opening 24 via the communication needle 10 to fill the septum chamber 28, 29 with medicament.

According to one embodiment, the needle assembly 2 also includes a plurality of hollow needles 34 that pierce the needle assembly septum 22, 30. In the first position of the needle assembly 2, all of the plurality of needles 34 pierces the inner and outer septums 22, 30 and none of the needles are exposed. Specifically, a sharpened proximal end 36 of each of the plurality of needles 34 is disposed in the inner septum 22 providing needle sterility.

In the second position of the needle assembly 2, one of the plurality of needles 34 is exposed for medicament delivery. In this instance, a proximal end of a selected needle 40 is disposed in the circular cavity 28 of the inner septum 22 to receive medicament. The second position of the needle assembly 2 is described in more detail below.

Figures 17, 18:
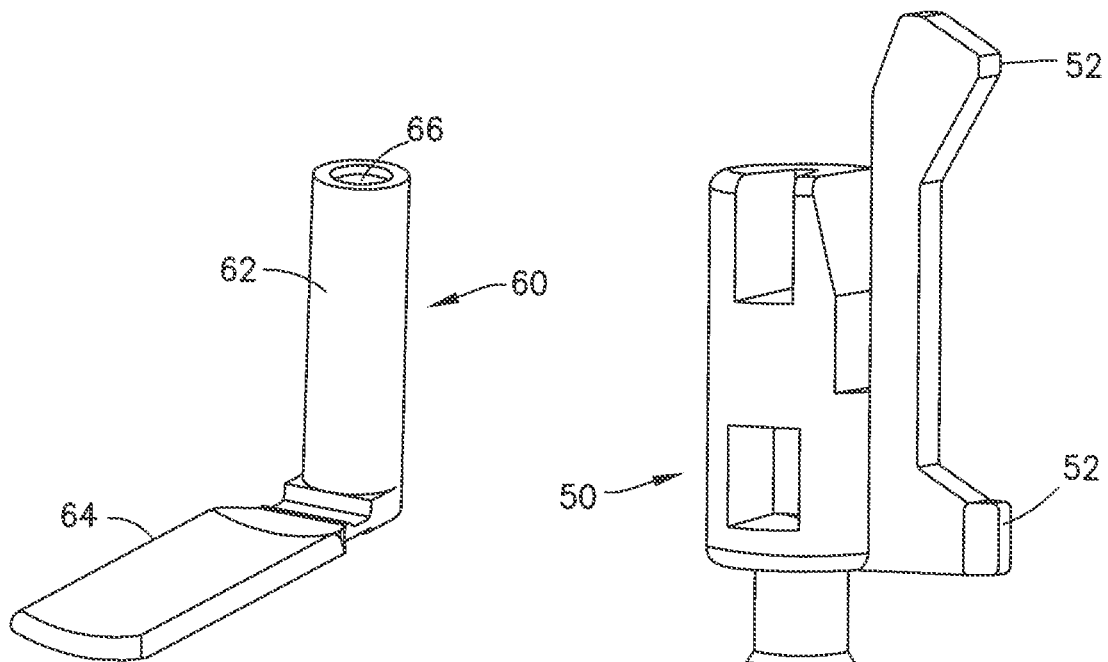
FIG. 17 illustrates a right perspective view of the peel tab.
FIG. 18 illustrates a left perspective view of a needle post.

According to one embodiment, each of the plurality of needles 34 is fixed to a needle post 50. Specifically, as illustrated in FIG. 18, each of the plurality of needles 32 enters a respective needle post 50 at a centerline of a needle post boss 54. Each of the plurality of needles 32 is preferably secured to the respective needle post 50 via adhesive, although other engagement means are contemplated.

FIG. 18 further illustrates the needle post 50 including needle post flanges 52. The needle post flanges 52 provide a means to secure the needle post 50 to the bottom cavity 14 of the frame 12. The plurality of needle post flanges 52 each engages the bottom cavity 14 of the frame 12 at a top position and a bottom position. Specifically, FIG. 6 illustrates the needle post 50 in the top position when the needle assembly is in the first position. FIG. 7 illustrates the needle post 50 in the bottom position when the needle assembly is in the second position. As illustrated in these Figures, the bottom cavity 14 provides two recesses for the needle post 50 to engage and be secured in the top and bottom positions.

The bottom cavity 14 of the frame 12 is designed to align the plurality of needle posts 50 according to the spike alignment protrusion 9. As a result, each of the plurality of needles 34 is disposed in the inner septum 22 and is aligned to the circular cavity 28 of the septum chamber 28, 29. Thus, the proximal end 36 of each of the plurality of needles 34 will enter into fluid communication with the septum cavity 28, 29 when used for medication delivery at the appropriate time.

As illustrated in FIG. 5, according to one embodiment, a peel tab 60 is disposed at a sharpened distal end 38 of each of the plurality of needles 34 in the first position of the needle assembly 2. The plurality of peel tabs 60 encloses and stores each of the needles 34 in a sterile environment prior to use and improves safety by protecting a user from inadvertent contact.

The plurality of peel tabs 60 is composed of a polymer layer, a composite layer of foil, a plastic material or a thermoplastic material. The plurality of peel tabs 60 is strong enough to pull the needle 34 into its distal position, but also able to have a living hinge at the flexible joint. The living hinge at the flexible joint allows the plurality of peel tabs 60 to bend and elastically recover in the manner illustrated in FIGS. 3, 4, and 6. Other materials satisfying the functionality of the plurality of peel tabs 60 are herein contemplated.

FIG. 17 illustrates that each of the plurality of peel tabs 60 includes a sterility barrier 62, a tab 64 and a peel tab hole 66. The distal end 38 of each of the plurality of needles 34 enters into a respective peel tab hole 66 of each of the plurality of peel tabs 60. The peel tab hole 66 engages and is secured to the needle post boss 54 via an annular snap fit or an interference fit, for example. The distal end 38 of each of the plurality of needles 34 is protected by the sterility barrier 62 being a hollow enclosure. The tab 64 is attached to a bottom exterior surface of the sterility barrier 62. The tab 64 is able to bend in a retracted (compact) position and an extended position to store the peel tab 60 when not in use and to remove the peel tab 60 from the needle.

Figure 13:
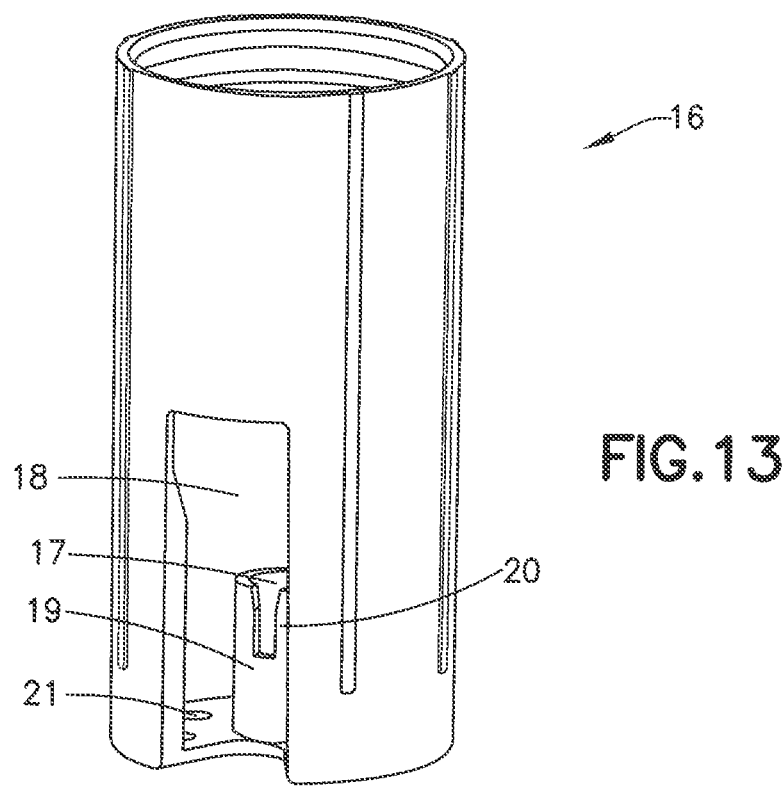
FIG. 13 illustrates a right perspective view of the selector ring.

The selector ring 16 houses all the components of the needle assembly 2. According to one embodiment, as illustrated in FIG. 13, the selector ring 16 includes a selector hole 17, a selector opening 18, a selector protrusion 19 having a protrusion slot 20 and a plurality of selector needle holes 21. As described above, the selector opening 18 provides access to each needle of the plurality of needles 34. Specifically, the selector opening 18 is sized to fit one peel tab 60. When the selector ring 16 rotates, only one peel tab 60 can be exposed through the selector opening 18 at a time. This feature advantageously prevents multiple needles from being simultaneously exposed for medication delivery.

At a bottom inner surface of the selector ring 16 is a selector protrusion 19 having a protrusion slot 20. The protrusion slot 20 engages the needle post 50 of the selected needle 40 in the second position of the needle assembly 2. Specifically, as the needle post 50 of the selected needle 40 moves downward to the bottom position, the needle post flange 52 enters into the protrusion slot 20. Since there is only one protrusion slot 20, only one needle post 50 and only one needle of the plurality of needles 34 enters into the second position of the needle assembly 2. Thus, the selector protrusion 19 advantageously prevents the needle posts 50 of the remaining needles of the plurality of needles 34 from moving to the bottom position.

The selector protrusion 19 includes a selector hole 17 being a hollow hole. The selector hole 17 is configured to allow the user to insert the cover 80 and move the needle assembly 2 from the second position to the first position. The plurality of selector needle holes 21 allows the user to determine which of the plurality of needles 34 have been used. Further description of this operation is described below.

The operation of the needle assembly 2 is now explained in an exemplary manner as follows. According to one embodiment, the user connects the needle assembly 2 to the medication delivery pen 4. When the user desires to use the needle assembly 2, the selector ring 16 is rotated to align with a peel tab 60 as illustrated in FIGS. 3 and 5. As illustrated in FIGS. 4 and 6, the user bends the tab 64 of the peel tab 60 of the selected needle 40 from a retracted, compact position to an extended position.

Next, the user pulls the tab 64 of the peel tab 60 of the selected needle 40 and moves the needle assembly 2 from the first position of FIG. 6 to the second position of FIG. 7. When the selected needle 40 is fully drawn out, the needle assembly 2 is in the second position. Subsequently, the sterility barrier 60 is removed from the selected needle 40 and the needle assembly 2 is ready for medicament delivery.

When the needle assembly 2 moves from the first position to the second position, the needle post 50 of the selected needle 40 moves from the top position to the bottom position in the bottom cavity 14 of the frame 12. When the needle post 50 of the selected needle 40 moves to the bottom position, the needle post flange 52 enters into the protrusion slot 20 of the selector protrusion 19 in the selector ring 16.

The user cannot rotate the selector ring 16 in the second position of the needle assembly 2. Moreover, none of the remaining needles of the plurality of needles 34 can be moved into the second position because the protrusion slot 20 is advantageously sized to fit one needle post 50. This configuration advantageously ensures that only one needle is exposed and used at a single time.

In the second position of the needle assembly 2, a proximal end 42 of the selected needle 40 also enters into fluid communication with the septum chamber 28, 29. A distal end 44 of the selected needle 40 exits the selector opening 17 of the selector ring 16 and is exposed for medication delivery. Accordingly, medicament is received by the proximal end 44 of the selected needle 40 and exits the distal end 44 of the selected needle 40 to be delivered to a patient.

When the first needle of the plurality of needles 34 is used, the circular cavity 28 and the longitudinal cavity 29 are filled with medicament, resulting in the needle assembly septum 22, 30 being primed. Specifically, medicament must traverse and fill the complete fluid path of the circular cavity 28 to reach the first needle of the plurality of needles 34. Accordingly, the incidence of air in the circular cavity 28 is advantageously reduced. Removing air from the fluid path also advantageously improves dose accuracy.

Figure 8:
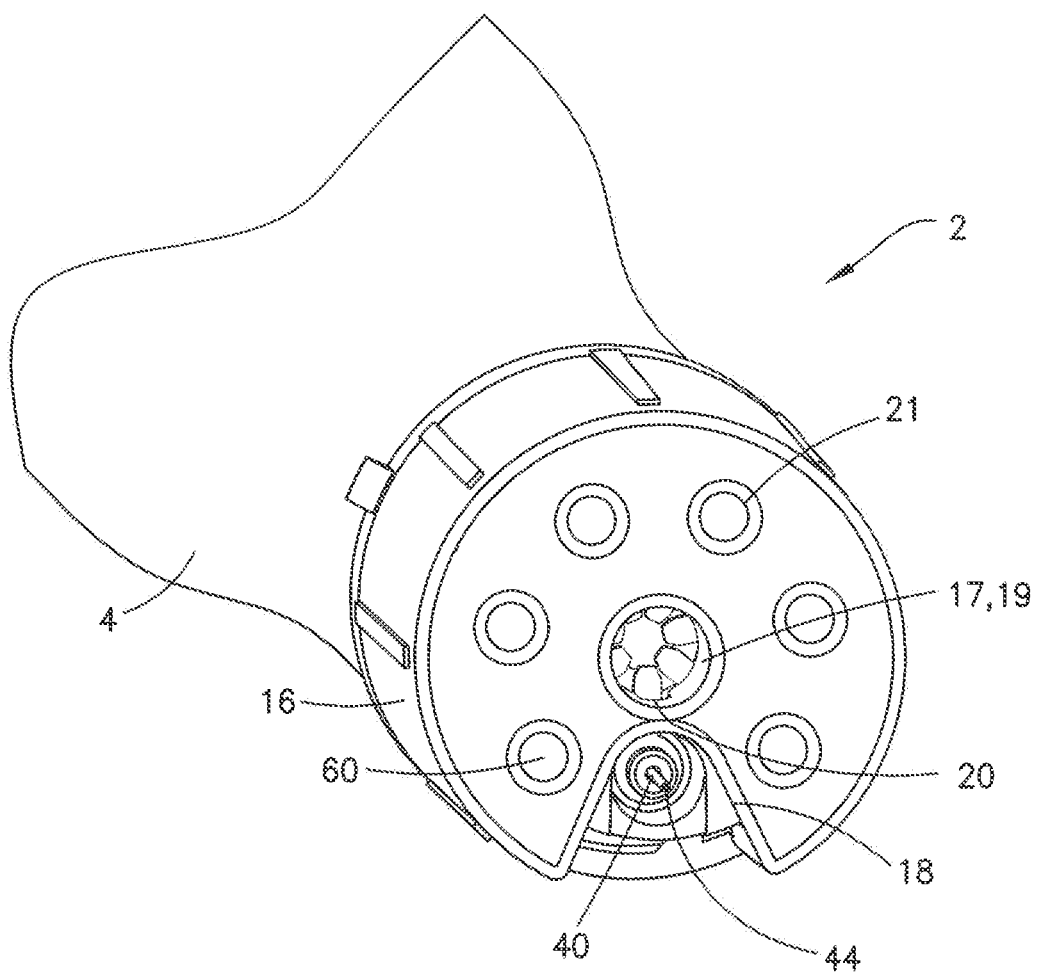
FIG. 8 illustrates a bottom left perspective view of the second position of the needle assembly.

FIG. 8 illustrates a bottom perspective view of the needle assembly 2 in the second position. The distal end 44 of the selected needle 40 is exposed through the selector opening 18 of the selector ring 16. The remaining unused needles are disposed in the needle selector 16 and protected by the peel tab 60. The remaining needles (used or unused) of the plurality of needles 34 and the associated needle posts 50 remain in the top position in the bottom cavity 14 of the frame 12. Specifically, the proximal ends 36 of the remaining plurality of needles 34 are sealed in the inner septum 22. The remaining plurality of needles 34 is not in fluid communication with the medicament stored in the circular cavity 28 of the inner septum 22. However, some portion of each of the remaining plurality of needles 34 contacts the medicament because the remaining plurality of needles 34 is aligned with the circular cavity 28 of the needle assembly septum 22, 30. The distal ends 38 of the remaining plurality of needles 34 are covered by the sterility barrier 60.

The plurality of selector needle holes 21 of the selector ring 16 provide a means to determine which of the plurality of needles 34 is already used. Specifically, the user can see if the distal end of the plurality of needles 34 is covered by the sterility barrier 62. If the sterility barrier 62 is visible, then that needle has not been used. On the other hand, if the sterility barrier 62 is not visible, then that needle has been used. FIG. 8 illustrates that five needles have not been used, one is currently in use and one has already been used.

Figure 9:
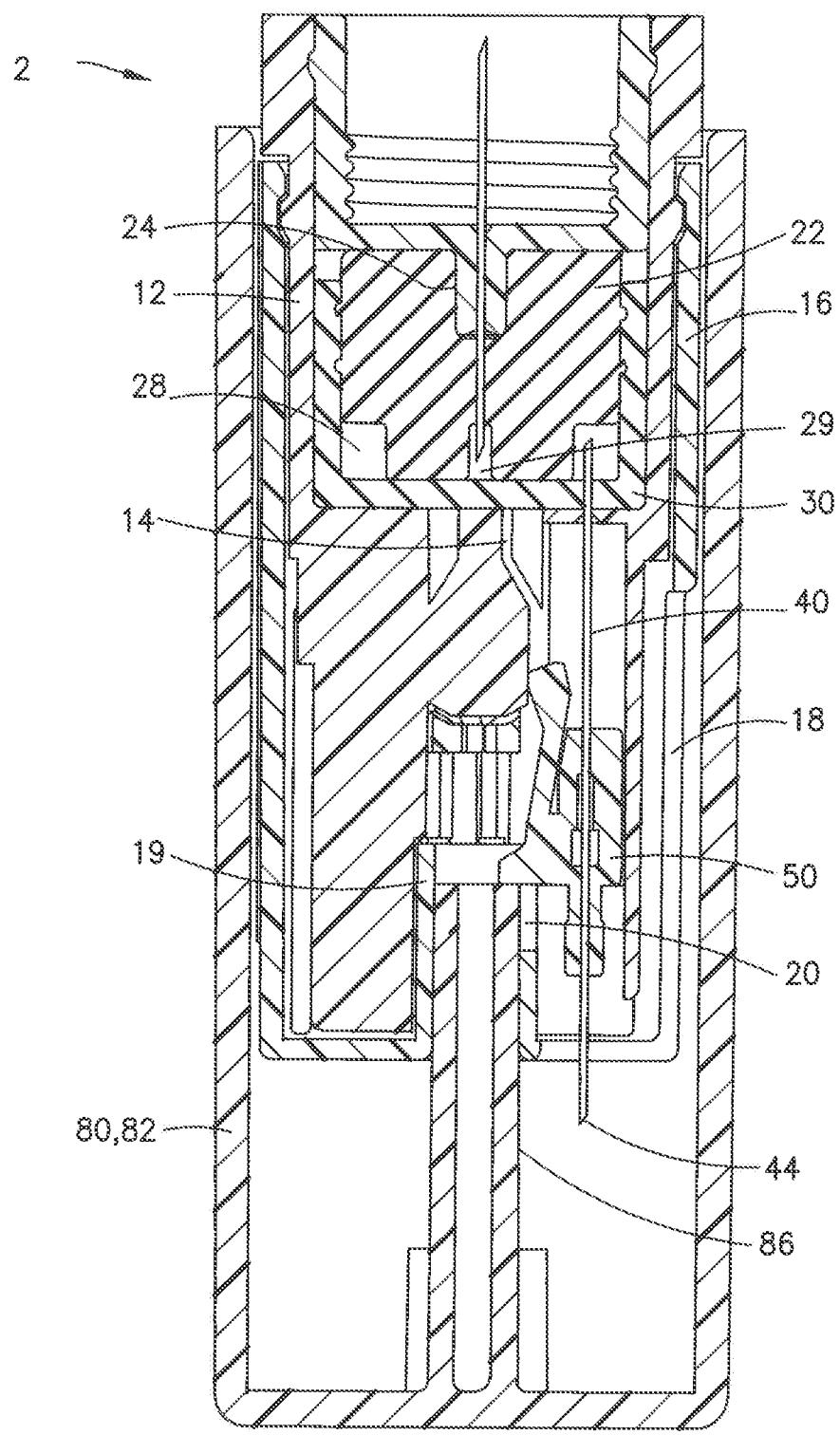
FIG. 9 illustrates a cross sectional view of the needle assembly returning from the second position to the first position via the cover.
Figure 10:
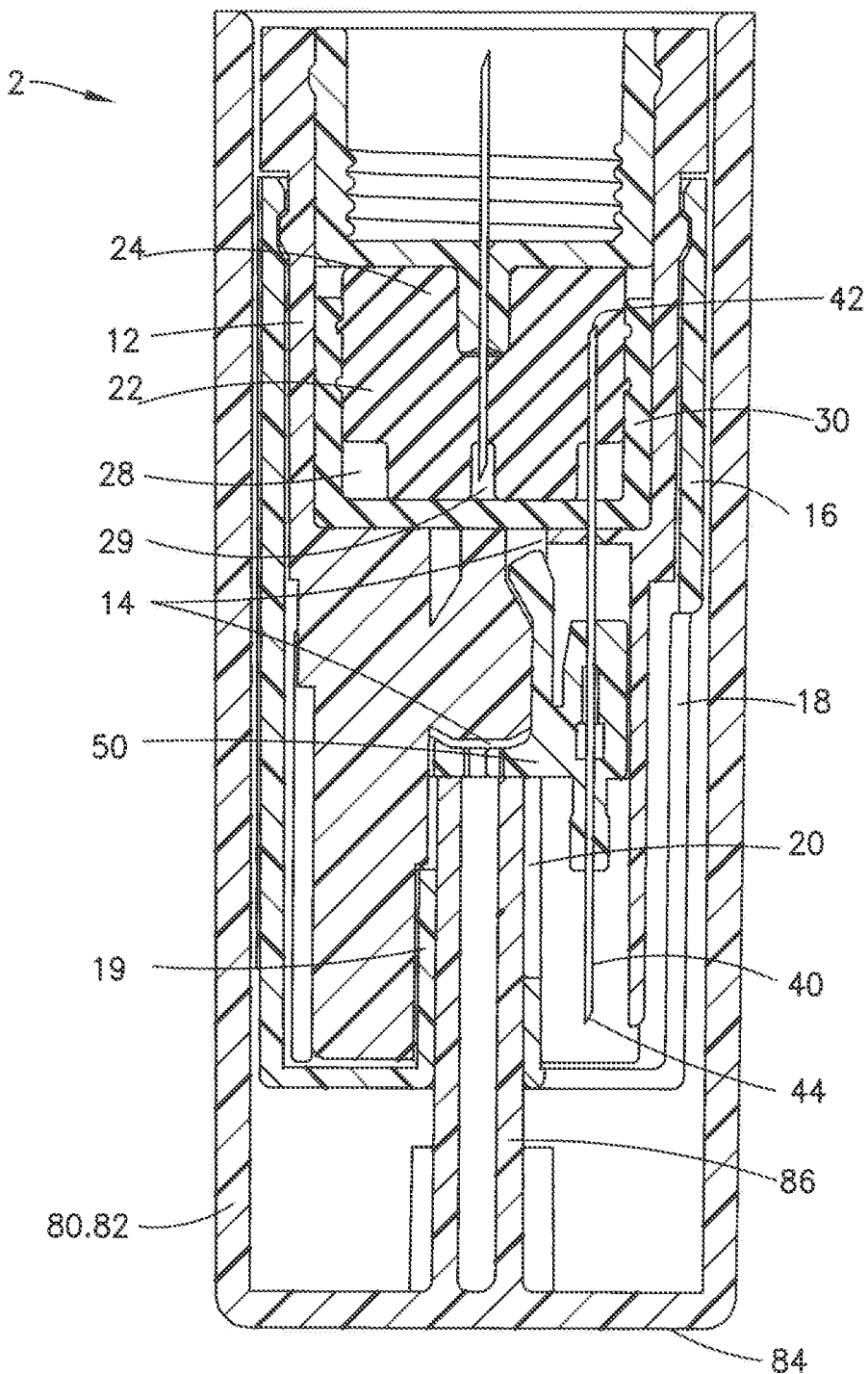
FIG. 10 illustrates a cross sectional view of the needle assembly returning to the first position via the cover.

FIGS. 9 and 10, according to one embodiment, illustrate the use of the cover 80 to return the needle assembly 2 from the second position to the first position. The cover 80 includes a cylinder 82, a base 84 and a protrusion 86. The cylinder 82 is configured to surround the needle assembly 2. The base 84 is configured to cover a bottom portion of the selector ring 16 of the needle assembly 2. The protrusion 86 extends from the base 84 and is disposed centrally within the cylinder 82. When the cover 80 is placed on the needle assembly 2, the protrusion 86 enters the selector hole 17. The protrusion 86 of the cover 80 applies pressure by pushing the needle post flange 52 of the needle post 50 of the selected needle 40 from the bottom position to the top position.

FIGS. 9 and 10 illustrate the protrusion 86 of the cover 80 moving the needle post 50 by applying pressure to the needle post flange 52. FIG. 9 illustrate the needle assembly 2 moving from the second position to the first position and FIG. 10 illustrates the second position of the needle assembly 2. These figures also illustrate that the needle post flanges 52 of each of the plurality of needles 34 are arranged toward a central axis of the selector ring 16. Such a configuration advantageously allows the protrusion 86 of the cover 80 to engage each of the plurality of needle posts flanges 52 to move the needle post 50 from the bottom position to the top position.

According to one embodiment, after the needle assembly 2 is returned to the first position, as illustrated in FIG. 10, the selected needle 40 can no longer be used. Since the selected needle 40 is no longer covered by the peel tab 60, the user cannot reuse the needle by pulling the selected needle 40 from the top position to the bottom position of the respective needle post 50. Such a configuration advantageously provides security and safety from inadvertent contact or use.

After the needle assembly 2 is returned to the first position, according to one embodiment, an adjacent needle is preferably selected for use. The selector ring 16 is then rotated to expose an adjacent peel tab 60 of the adjacent needle. However, the user has the flexibility to expose and choose any of the remaining plurality of peel tabs 60.

Once a needle and respective peel tab 60 is selected, the selected peel tab 60 is removed for operation in the manner described above. The selected needle 40 is then used for medication delivery and afterwards, the cover 80 is used to return the selected needle 40 to the first position of the needle assembly 2. These steps are repeated until all of the plurality of needles 34 is used. The combination of the selector ring 16 and the plurality of peel tabs 60 simplify the needle assembly 2, allow for easy to use operation and improve safety.

During operation, although the selected needle 40 moves axially, the selected needle 40 does not move radially. In fact, none of the plurality of needles 34 substantially moves radially or rotates at any point during operation. No substantial radial or rotational movement in this regard is understood as 0±5% with respect to a center axis of the needle assembly 2. Preferably, one skilled in the art understands that substantial in this context means that no radial of rotational movement is required to perform the intended function. Slight radial or rotational movement is desired to ensure the proper spacing of parts for smooth operation and proper movement of the needles axially without jamming.

Each of the plurality of needles 34 is advantageously isolated from the septum of the medication delivery pen 4 throughout the operation of the needle assembly 2. Such an arrangement advantageously provides simplicity in design, improves sterility and provides a separation between a patient end and a non-patient end.

Figure 19:
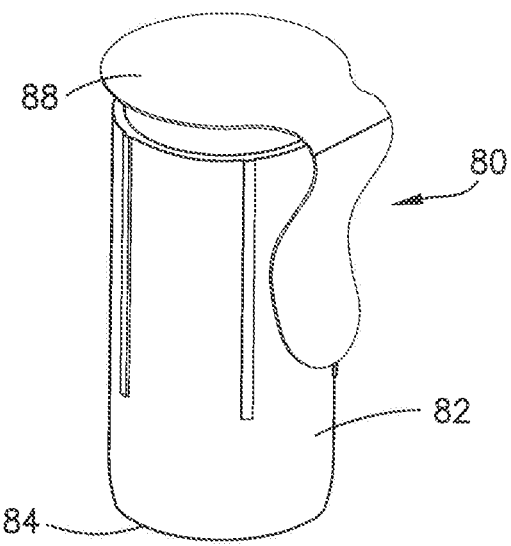
FIG. 19 illustrates a left perspective view of the needle assembly in the cover and sealed by a teardrop label.

According to one embodiment, FIG. 19 illustrates the cover 80 enclosing the needle assembly 2. The cover 80 is sealed with a teardrop label 88 to seal the needle assembly 2 and maintain its sterility for transportation and security purposes prior to operating with the medication delivery pen 4. When the needle assembly 2 is ready for use, the user peels off the teardrop label 88 and removes the needle assembly 2 from the cover 80.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to arty particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An attachable needle assembly for use on a medication delivery pen, the needle assembly comprising:
    a communication needle that is configured to pierce a reservoir septum of the medication delivery pen;
    a spike housing surrounding the communication needle and configured to engage the medication delivery pen;
    a selector ring including a selector opening, the selector ring enclosing:
        a septum of the needle assembly defining a septum chamber, the septum chamber of the needle assembly being in continuous fluid communication with the communication needle;
        a plurality of needles disposed in the septum of the needle assembly; and
        a peel tab enclosing each of the plurality of needles, wherein
    the selector opening of the selector ring is configured to align with a selected peel tab of the plurality of peel tabs corresponding to a selected needle of the plurality of needles,
    the selected peel tab is configured to be drawn out of the selector ring and move the selected needle from a first position of the needle assembly to a second position of the needle assembly, and
    the selected needle enters into fluid communication with the communication needle in the second position.

2. The attachable needle assembly of claim 1, wherein the septum including an inner septum and an outer septum, the inner septum is sealed within the outer septum.

3. The attachable needle assembly of claim 2, wherein the inner septum includes the septum chamber and the septum chamber comprising a circular cavity that carries medicament from the communication needle and fluidly communicates with the selected needle of the plurality of needles in the second position.

4. The attachable needle assembly of claim 1, wherein in the first position, each of a proximal end of the plurality of needles is not in fluid communication with the septum chamber and each of a distal end of the plurality of needles is disposed in a respective peel tab of the plurality of peel tabs.

5. The attachable needle assembly of claim 1, wherein in the second position, a proximal end of the selected needle of the plurality of needles is in fluid communication with the septum chamber.

6. The attachable needle assembly of claim 1, wherein in the second position, the selected peel tab is removed from a distal end of the selected needle of the plurality of needles to expose the selected needle.

7. The attachable needle assembly of claim 1, wherein in the second position, a proximal end of each of a remaining plurality of needles is not in fluid communication with the septum chamber.

8. The attachable needle assembly of claim 1, wherein
    each of the plurality of needles is secured in a needle post; and
    each of the plurality of needle posts axially moves in the selector ring and is engaged to the selector ring in a top position and a bottom position.

9. The attachable needle assembly of claim 1, wherein in the first position, each of the plurality of peel tabs is connected to a respective needle post of each of the plurality of needles.

10. The attachable needle assembly of claim 1, wherein
    the selector ring includes a slotted protrusion; and
    a needle post of the selected needle enters into a slot of the slotted protrusion of the selector ring in the second position.

11. The attachable needle assembly of claim 10, wherein a needle post of each of the respective remaining plurality of needles is offset from the slot of the slotted protrusion causing the remaining plurality of needles to remain in a top position.

12. The attachable needle assembly of claim 1, wherein the selector opening of the selector ring is aligned with one peel tab at a time.

13. The attachable needle assembly of claim 1, wherein the selector ring further encloses a frame that carries each of a plurality of needle posts.

14. The attachable needle assembly of claim 1, wherein the plurality of needles is seven needles.

15. The attachable needle assembly of claim 1, wherein the selector ring is rotatable with respect to the plurality of needles.

16. The attachable needle assembly of claim 1, wherein the plurality of needles do not pierce the reservoir septum of the medication delivery pen.

17. The attachable needle assembly of claim 1, wherein the plurality of needles only move axially and do not substantially move radially and do not substantially rotate.

18. The attachable needle assembly of claim 1, further including
    a cover enclosing the needle assembly; and
    a label sealing and maintaining sterility of the needle assembly in the cover prior to operating with the medication delivery pen.

19. The attachable needle assembly of claim 1, wherein a cover applies pressure to the selected needle of the plurality of needles to return the needle assembly from the second position to the first position.

20. The attachable needle assembly of claim 19, wherein
    the cover includes
        a cylinder;
        a base; and
        a protrusion extending from the base and disposed within the cylinder, and
    the protrusion engages the selector ring to apply pressure to the selected needle of the plurality of needles to return the needle assembly from the second position to the first position.

21. The attachable needle assembly of claim 1, wherein when the selected needle of the plurality of needles returns from the second position to the first position of the needle assembly, the needle is unable to be reused.

22. A method of operating an attachable needle assembly on a medication delivery pen, the method comprising:

piercing a reservoir septum of the medication delivery pen;
engaging the medication delivery pen;
establishing fluid communication between the medication delivery pen and the needle assembly;
disposing a plurality of needles in a septum of the needle assembly; and
enclosing each of the plurality of needles with a peel tab, wherein
a portion of the needle assembly is aligned with a selected peel tab of the plurality of peel tabs corresponding to a selected needle of the plurality of needles, the selected peel tab is drawn out of the needle assembly and moves the selected needle from a first position of the needle assembly to a second position of the needle assembly, and the selected needle enters into fluid communication with the medication delivery pen in the second position.

\* \* \* \* \*